United States Patent [19]

Chappel et al.

[11] Patent Number: 5,352,779
[45] Date of Patent: Oct. 4, 1994

[54] SITE-DIRECTED MUTAGENESIS MODIFIED DNA ENCODING GLYCOPROTEIN HORMONES AND METHODS OF USE

[75] Inventors: Scott C. Chappel; Edward G. Bernstine, both of Boston, Mass.

[73] Assignee: Applied Research Systems ARS Holding N.V., Curacao, Netherlands

[21] Appl. No.: 126,134

[22] Filed: Sep. 23, 1993

Related U.S. Application Data

[62] Division of Ser. No. 136,236, Dec. 21, 1987, Pat. No. 5,260,421.

[51] Int. Cl.$^5$ ............................................. C12N 15/18
[52] U.S. Cl. ................................. 536/23.51; 536/23.5; 435/69.1; 435/69.4; 435/320.1; 435/252.3; 530/399
[58] Field of Search .................... 536/23.5, 23.51; 435/69.1, 69.4, 320.1, 252.3; 530/399

[56] References Cited

U.S. PATENT DOCUMENTS

| | | | |
|---|---|---|---|
| 4,868,119 | 9/1989 | Clark et al. | 435/240.2 |
| 4,879,227 | 11/1989 | Clark et al. | 435/70 |
| 5,260,421 | 11/1993 | Chappel et al. | 530/397 |

FOREIGN PATENT DOCUMENTS 0009800  7/1990  World Int. Prop. O. .

OTHER PUBLICATIONS

Slbok et al *Biochemistry* 26: 3650 (1987).
Matzuk et al *J. Cell Biol* 106:1049 (1988).
Matzuk et al *J Biol Chen* 264:2409 (1989).

*Primary Examiner*—Robert J. Hill, Jr.
*Assistant Examiner*—Shelly Guest Cermak
*Attorney, Agent, or Firm*—Browdy and Neimark

[57] ABSTRACT

Described are new glycoprotein hormones capable of competing with natural hormones for the normal receptor binding sites but substantially incapable of effecting post receptor activities. The glycoprotein hormones of the present invention have had specific (rather than all) oligosaccharide chains removed so as to effectively diminish biologic activity while not significantly reducing plasma half-life, thus improving the molecules effectiveness as an antagonist compared with conventionally-produced molecules. The preferred glycoprotein hormones are ideally obtained by site-directed mutagenesis to selectively deglycosylate the protein. Also described are therapeutic treatments comprising the administration of the recombinant glycoprotein hormones of the present invention as hormone antagonists.

4 Claims, No Drawings

SITE-DIRECTED MUTAGENESIS MODIFIED DNA ENCODING GLYCOPROTEIN HORMONES AND METHODS OF USE

CROSS-REFERENCE TO RELATED APPLICATION

The present application is a divisional of U.S. application Ser. No. 07/136,236, filed Dec. 21, 1987, now U.S. Pat. No. 5,260,421.

FIELD OF THE INVENTION

This invention relates generally to hormones and more particularly to glycoprotein hormones including the pituitary glycoproteins, and further provides methods for creating hormone analogs by site-directed mutagenesis.

BACKGROUND OF THE INVENTION

Glycoprotein hormones, especially those synthesized and secreted by the anterior pituitary gland, play critically important roles in a variety of bodily functions including: metabolism, temperature regulation, growth, and reproduction. The pituitary glycoproteins, luteinizing hormone (LH), follicle stimulating hormone (FSH), and thyroid stimulating hormone (TSH) are similar in structure to the placental gonadotropin, human chorionic gonadotropin (hCG). Each of the molecules is actually a dimer consisting of two protein chains held together by non-covalent, ionic interactions. The alpha chain for each of the hormones is identical. The beta chain is the hormone-specific portion of the dimer.

Following secretion, the hormones travel in the blood stream to the target cells which contain membrane bound receptors. The hormone binds to the receptor and stimulates the cell. Typically, such stimulation involves an increase in activity of a specific intracellular regulatory enzyme which in turn catalyzes a biochemical reaction essential to the response of the cell. In the case of hCG, binding to the hCG receptor present upon the corpus luteum (an ovarian structure), stimulates the activity of the enzyme adenylate cyclase. This enzyme catalyzes the conversion of intracellular ATP to cyclic AMP (cAMP). cAMP stimulates the activity of other enzymes involved in the production of ovarian steroid hormones, especially progesterone hCG-stimulated progesterone secretion is essential for the maintenance of pregnancy during the first trimester of gestation.

The exact mechanism by which a dimeric glycoprotein hormone, such as hCG, stimulates post-receptor events, such as activation of adenylate cyclase activity, is unknown. By a variety of experimental manipulations, it has been shown, however, that the carbohydrate structures, each attached to the hCG molecule by a linkage at respective asparagine residues (N-linked), play important roles in this regard. Treatment of glycoprotein hormones, such as LH, FSH, or hCG with hydrogen fluoride removes approximately 70 percent of the oligosaccharide side chains. The resultant partially deglycosylated molecules retain their receptor binding activity but are unable to stimulate any post-receptor events. Thus it is clear that the sugar portion of the glycoprotein hormone, while not directly involved with receptor binding, plays a critical role in post-receptor events, and therefore, biologicactivity.

It is also known that in addition to a role in the in vitro bioactivity, oligosaccharides are important components of the molecule's survival time in circulation. Indeed, plasma half-life of a glycoprotein hormone is directly related to the amount of one particular sugar molecule, sialic acid, generally present upon the most distal portion of the oligosaccharide chain. The removals of the carbohydrate portions (by hydrogen fluoride treatment) would result in the production of hormones that bind to the receptor but fail to exert the expected biologic response. In addition, these molecules would have an extremely short plasma half-life since the lack of terminal sialic acid residues would increase the binding affinity to the hepatic asialoglycoprotein receptor thereby hastening clearance from the systemic circulation.

Many clinical endocrinopathies are the result of over production of stimulating hormones (e.g., excess TSH secretion resulting in hyperthyroidism). A conventional treatment for a pathologic state caused by a hormone excess would be the administration of a hormone antagonist. To be effective, an antagonist must bind with high affinity to the receptor but fail to activate post receptor events. From the earlier discussion, it can be anticipated that hydrogen fluoride treated hormones (that have had approximately 70 percent of carbohydrates removed) would be effective, competitive antagonists. Indeed, it has been shown that HF-treated hormones bind with somewhat greater affinity for the biologic receptor, compete effectively with native material, and diminish the expected biologic action of native hormone in a dose-dependent fashion.

At first glance, such a hormone preparation would appear to be a viable candidate for a competitive antagonist therapeutic agent. However, four problems are associated with large scale production of such preparations. First, all pituitary hormone preparations are generally contaminated with other hormones. Thus, while it may be possible to obtain a preparation of a hormone and partially deglycosylate it; the resultant preparation would also contain other deglycosylated hormones as contaminants which may disadvantageously produce unwanted and unacceptable side effects following administration. Secondly, preparations of partially purified hormones vary greatly in their potency, physicochemical characteristics and purity. Therefore, each batch produced would need to be analyzed carefully. The possibility of batch-to-batch variability would necessitate repeated execution of clinical trials to determine the effective dose. Thirdly, the method used to deglycosylate is incomplete and, therefore, somewhat uncontrollable. No information is available as to the variability associated with hydrogen fluoride treatment of successive batches of hormone. Potential variability in this process would also require extensive characterization of each batch produced. Fourth, carbohydrate side chains also play an important role in dictating the plasma half-life of a molecule. Partially deglycosylated hormones have been shown to be rapidly cleared from the circulation following injection. Therefore, repeated injections of large doses of deglycosylated hormones would be required to achieve a desired effect. The need for such large doses of hormone to deglycosylate and administer creates yet another problem, namely availability. Large quantities of hormones are presently unavailable and could conceivably only be made available through recombinant DNA technology.

As mentioned above, deglycosylated hormones, while exhibiting the desired competitive antagonistic properties in vitro would be of little therapeutic value in vivo due to their extremely short plasma half-life. The only potential solution to this dilemma would be to preferentially remove carbohydrate residues that are responsible for imparting the molecules' biologic action and sparing those that provided the molecules' long plasma half-life. It is, however, impossible to obtain this result with conventional chemical or enzymatic means (i.e. hydrogen fluoride treatment or enzymatic digestion) because of the non-specific nature of the chemical treatment.

It is an object of the present invention to provide a method for preferentially removing carbohydrate residues that are responsible for imparting biologic action to molecules while sparing those associated with a long plasma half-life.

It is yet another object of the present invention to provide a method of for obtaining molecules via non-chemical treatment which have the desired antagonistic nature coupled with a long half-life.

It is still another object of the present invention to provide a recombinant technique for obtaining therapeutically effective glycoprotein hormones having-been partially deglycosylated by having at least one oligosaccharide chain entirely removed.

It is still yet another object of, the present invention to provide novel hormonal cornperitive antagonists having therapeutic utility.

It is yet still another object of the present invention to provide competitive hormone antagonists having substantially batch-to-batch uniformity and consistent potency.

SUMMARY OF THE INVENTION

In accordance with the principles and objects of the present invention, there are provided methods for creating antagonistic molecules by removing specific glycosylation sites normally present on the molecule through a recombinant DNA technique called site-directed mutagenesis. Specifically, the method of the present invention employs the fact that N-linked oligosaccharides attach to the protein portion of hormones at asparagine residues only when such asparagine residues are present in the carbohydrate attachment signalling sequence: asparagine—any amino acid—threonine or serine. The method of the instant invention advantageously eliminates the glycosylation site by changing the nucleotide sequence of the gene that codes for the hormone. This is advantageously accomplished by mutating the codon for asparagine residues to some other amino acid, preferably one that preserves the overall charge of the protein or, alternatively, changing the threonine or serine codon to another amino acid thereby removing the glycosylation signal. The resultant expressed protein hormone will be completely lacking the sugar normally present at the now altered glycosylation site thereby rendering it a competitive antagonist.

Advantageously, the method allows for the continued specific existence of other carbohydrate attachment points for prolonging the plasma half-life of the molecule without disadvantageously affecting transduction of the post-receptor bioactivity. Accordingly, and unlike prior methods, the instant invention can provide a large quantity of uniform quality, competitive hormone antagonist with a long plasma half-life. The invention further comprises therapeutically effective formulations of these modified molecules including pharmaceutically acceptable salts thereof and also any combination of the foregoing with a carrier vehicle ideally selected to aid in the administration of the molecule to a mammal or other animal without deleteriously affecting either the molecule or the animal.

Certain specific hormones of the instant invention may also be advantageously employed as safe and effective first-trimester abortifacients. After a newly ovulated egg is fertilized within the oviducts, it travels to the uterus where it implants in the innermost layer, the endometrium. Shortly after implantation, the trophoectodermal layers differentiate into chorionic villi which are finger-like projections that "root" deeper within the endometrial layer. As the chorionic villigrow, one cell type within them begins to manufacture large amounts of hCG. Until these villi differentiate and proliferate into a placenta with steroidogenic capacity, the hCG that is secreted travels to the ovary to "rescue" the corpus luteum from its programmed demise by maintaining its steroidogenic capacity. Additionally, hCG stimulates the continued secretion of progesterone which prevents uterine contractility and sloughing of the endometrium (menstruation) which would otherwise terminate pregnancy. In contrast, failure to maintain adequate serum progesterone levels results in spontaneous abortion until after the first trimester of pregnancy when the placenta begins to supply adequate progesterone to maintain the conceptus. Thus treatment of pregnant women, during the first trimester, with an hCG competitive antagonist of the present invention will result in a failure of endogenous hCG to maintain the corpus luteum, thereby resulting in a falling serum progesterone levels and abortion.

DETAILED DESCRIPTION OF THE INVENTION AND BEST MODE

Site-directed mutagenesis provides a powerful technique for generating defined point mutants. The general procedure, is described by Zoller, M. O. and Smith, M. (1982) Nucl. Acids Res. 10, 6487–6500 and is summarized as follows: The DNA fragment of interest is cloned into an M13 derived vector and single-stranded DNA (ssDNA) is prepared. A synthetic oligonucleotide, usually 18 ±2 bases long and complementary to a region of the ssDNA except for a mismatch which will direct the mutagenesis, is used as a primer. The template and primer are annealed. Large fragment E. coli DNA Polymerase I (Klenow), deoxyribonucleotides and T4 DNA ligase are added and closed circular double-standard DNA (ccDNA) is synthesized and ligated. Enrichment for ccDNA is done by one of several methods. The enriched ccDNA is transfected with competent JM101 cells and a population of both mutant and wild-type molecules are obtained. Any of a variety of well known screening procedures may be advantageously used to differentiate between the mutant and wild-type molecules. The mutant molecule is then isolated and confirmed by sequencing.

There are several points to consider when employing this method. It is highly desirable to do a thorough computer search with the proposed oligonucleotide to ensure specific priming at the desired site. The oligonucleotide should be checked against the M13 vector and the DNA fragment to be mutagenized to be certain this is the case. Another potential difficulty preferably avoided is the increased background of wild-type molecules resulting from inefficient conversion of ssDNA to ds ccDNA. Zoller and Smith reference several methods available to overcome this potential problem. Zoller and Smith, themselves, employed alkaline sucrose gradients for their enrichment. Similarly, S1 nuclease treatment may be used.

In designing the mutagenic oligonucleotide, it is preferable either to create or destroy a restriction enzyme site where possible. By so doing the screening for mutant DNA is greatly facilitated by a simple restriction site-fragment size analysis.

If the creation or destruction of suitable restriction sites is not possible, screening may be accomplished by a hybridization assay technique using the mutagenic oligonucleotide as a probe. This latter method is advantageously independent of the mutation position and can be done using either phage or isolated DNA. The principle of the hybridization assay is that the mutagenic oligonucleotide will form a more stable duplex with the mutant DNA because they match perfectly; whereas, the wild-type has mismatching and thus a lower level of complementarity. Advantageously, the hybridization is initially carried out under conditions of low stringency so that both the mutant and wild-type hybridize to the $^{32}$P-labeled oligonucleotide. The filters are then washed at increasingly higher temperatures until only the mutants hybridize. This method is very rapid and can be usually carried out in one day. While an isotopic label has been suggested for the probe, other labels may be employed although other labels are generally not as detectable as isotopic labels at very low levels.

EXAMPLE 1

Site-Selection

There are two glycosylation sites in the human α subunit, occurring at amino acid positions 52 and 78. The present invention directs that the amino acid sequence at these positions, Asn-X-Thr be changed to Asn-X-Val, Asn-X-Met or Gln-X-Thr. For "α52", there are several possible mutations that fit the above scheme all involving 2 base mismatches. The codon used for Thr at position 54 is ACC. The codons for Val are GTT, GTC, GTA and GTG; for Met, ATG. So the possibilities are ACC-GTC or ACC-ATG. AAC codes for Asn at amino acid 52 and changing this to Gln (CAA or CAG) again involves a 2 base mismatch. Unfortunately, none of the above mutations creates a restriction enzyme site. Several sites are destroyed but these are very common and provide no useful screening information.

For "α78", there are two potential choices for mutation of Thr <ACG). To change this codon to Met, ATG, requires a one base substitution. For Val, GTG, a double mutation is necessary. The Asn-Gln conversion requires the same changes as in α52. Again, no restriction sites are created nor are any destroyed at these positions. However, and as noted previously, a 2 base mismatch will be easier to screen for the mutant since there will be greater homology for its' oligonucleotide than for the wild-type.

Preferred embodiment for the conversion of the Thr-Met for α78 is given below.

```
                    Asn His Met Ala Cys
mutant . . .        AG AAC CAC ATG GCG TGC C
                5'                            3'

α78             AG AAC CAC ACG GCG TGC C
                    Asn His Thr Ala Cys
```

```
oligo           TCTTGGTG TAC CGCACGG
            3'                          5'
```

EXAMPLE 2

Materials

M13mp18 and mp19RF, IPTG, XGal and phenol were obtained from BRL (Bethesda Research Laboratories). T4 DNA ligase, T4 polynucleotide kinase, all restriction endonucleases and *E. coli* DNA polymerase I large fragment K-lenow were purchased from New England Biolabs. ATP was obtained from Sigma. $\gamma^{32}$P-ATP and $\alpha^{32}$P-ATP were purchased from DuPont/NEN Medical Products. PEG-6000 was obtained from Kodak. Acrylamide, bis-acrylamide and TEMED were purchased from BioRad. S1 nuclease, ribonuclease A and *E. coli* tRNA was obtained from Boehringer Mannheim. Deoxyribonucleotide triphosphates, pUC 18 and pUC 19 plasmids were purchased from PL-Pharmacia. Nitrocellulose filters were obtained from Schleicher and Schuell.

Buffers, Media and Stock Solutions

| Buffers | |
|---|---|
| 10x kinase | 500 mM Tris—Cl(7.5) |
| | 100 mM MgCl$_2$ |
| | 10 mM DTT |
| | 1 mM spermidine |
| | 1 mM EDTA |
| 10x ligase | 500 mM Tris—Cl(7.5) |
| | 100 mM MgCl$_2$ |
| | 10 mM DTT |
| 10x ATP | 10 mM ATP, pH 7.0 |
| 10x dNTP's | 2 mM dATP, 2 mM dCTP, 2 mM dGTP, |
| | 2 mM DTTP |
| | pH 7.0 |
| S1"stop" | 50 mM Tris base |
| | 20 mM EDTA |
| | 1ug carrier tRNA |
| 10x S1 | 300 mM NaOAC (4.5) |
| | 500 mM NaCl |
| | 45 mM ZnSO$_4$ |
| 1x TE | 10 mM Tris—Cl(8.0) |
| | 1 mM EDTA |
| Solution A | 200 mM Tris—Cl(7.5) |
| | 100 mM MgCl$_2$ |
| | 500 mM NaCl |
| | 10 mM DTT |
| 50x Denhardt's | 1% Ficoll |
| | 1% Polyvinylpyrrilidone |
| | 1% BSA |
| 1x SSC | 150 mM NaCl |
| | 15 mM Na citrate |
| Media | |
| 5x M9 Salts | 10.5 g/L K$_2$HPO$_4$ |
| | 4.5 g/L KH$_2$PO$_4$ |
| | 1.0 g/L (NH$_4$)$_2$ SO$_4$ |
| | 0.5 g/L Na citrate |
| | Autoclave and temper at 55° C. |
| | Add, with sterile technique: 1 ml |
| | 1M MgSO$_4$.7 H$_2$O; 0.7 ml 0.7% |
| | thiamine, 10 ml 20% glucose. |

Minimal Media Plates

Add 15g bactogar to 800 ml ddH$_2$O, autoclave. After tempering to 55° C., add 200 ml 5×M9 and pour plates.

YT 8 g/L bactotryptone
5 g/L yeast extract
5 g/L NaCl

Autoclave

EXAMPLE 3

Preparation of ssDNA

The desired DNA fragment encoding for the alpha subunit was digested with the appropriate restriction enzyme and isolated from a polyacryl amide gel. The fragment was ligated into the appropriate site in the M13 vector of choice via conventional techniques. Approximately 300ng of fragment and 30ng digested M13 were mixed in 10x ligase buffer, 10x ATP and 400U T4 DNA ligase in a total volume of 50ul. The ligation reaction was incubated for four to six hours at room temperature or alternately it can be incubated for 20 hours at 16° C.

A loopful of JM101 cells was transferred from a M9 minimal plate to a flask containing the appropriate volume of YT and grown to a density of $OD_{660}=0.3-0.4$ at 37° C. with aeration. The cells were collected by centrifugation in a Sorvall SS-34 at 8,000rpm for ten minutes at 4° C., immediately resuspended in 0.5 volumes of ice-cold 50mM $CaCl_2$ and kept on ice for 20 minutes. The cells were centrifuged again and resuspended in 1/10 volume original growth volume with chilled 50mM $CaCl_2$. The competent cells are left on ice until ready to use.

Aliquots of the ligation reaction were added to the JM101 competent cells and transfected as described by Messing, J. (1984) Methods Enzm. 101, 20. ssDNA was prepared from individual plaques by growing 5 ml YT cultures with 50ul exponential JM101 for six to eight hours at 37° C. The cells were centrifuged at 3000rpm for ten minutes at 4° C. and 4 ml supernatants were transferred to clean Corex tubes. PEG, NaCl and RNaseA were added to final concentrations of 4%, 500mM and 10ug/ml, respectively. The tubes were incubated at room temperature for 15 minutes. The solutions were then centrifuged at 8,000rpm for 10 to 15 minutes at 40° C. in the SS-34 rotor. The supernatants were decanted and the pellets resuspended in 300ul 1x TE and transferred to microcentrifuge Eppendorf tubes. A TE-saturated phenol, then ether extractions were done, followed by ethanol precipitation with 1/10 volume 3M NaOAC, pH 5.2. The dried pellet was re-suspended in TE. A recombinant with the desired orientation was then chosen and a one liter culture of ssDNA was prepared by scaling-up the above method. This ssDNA served as template source for all mutagenesis experiments.

EXAMPLE 4

5' Phosphorylation of the Oligonucleotide

For mutagenesis: 1000-3000 pmol of oligonucleotide was phosphorylated in a solution containing 2ul 10x kinase buffer, 2ul 10x ATP and 4U polynucleotide kinase in a total volume of 20ul. The reaction was incubated at 37° C. for 30-60 minutes and terminated by incubation at 650° C. for 10 minutes.

For hybridization: The oligonucleotide was phosphorylated as above in a volume of 50ul using 50-10-0uCi $\gamma^{32}$P-ATP as the only source of ATP. To remove unincorporated nucleotide, the reaction was precipitated with a ½ volume 7.5M $NH_4OAc$ and three volumes of cold ethanol. The pellet was washed several times with cold 70% ethanol, dried, and resuspended in 50ul TE.

EXAMPLE 5

Oligonucleotide—directed synthesis of ds ccDNA

Annealing: Approximately 13 pmol of ssDNA, 260 pmol 5' phosphorylated oligonucleotide and 1ul of solution A were mixed in a total volume of 10ul. As a control, the above was done without the oligonucleotide. The reactions were incubated at 55° C. for five minutes, then 22° C. for five minutes.

Extension: 1.5ul 10x Klenow buffer, 1.5ul 10x dNTP's and 5U Klenow were added: to the annealing reactions in a final volume of 15ul. These reactions were incubated for five minutes at 22° C.

Ligation: To the above reactions, 1ul 10x ligase, 2ul 10x ATP and 400U T4 DNA ligase were added to a final volume of 20ul. The reactions were incubated for 20 hours at 16° C.

EXAMPLE 6

Enrichment for ccDNA

To the ligation reaction, 3ul 10x S1 buffer and 0.9U S1 nucl ease were added to a final volume of 30ul. A 15ul aliquot was immediately removed into a 1.5 ml Eppendorf tube containing 40ul S1 "stop" buffer. The S1 nuclease reaction was allowed to proceed for three minutes at room temperature. After three minutes, 40ul "stop" buffer was added to the original reaction eppendorf. The reactions were phenol:$CHCl_3$ extracted and ethanol precipitated. The pellets were then resuspended in TE.

EXAMPLE 7

Transfection of ccDNA

Aliquots of the ligation reactions were used to transfect competent JM101 cells as previously described.

EXAMPLE 8

Screening

A dry nitrocellulose filter was carefully placed on top of each transfection plate and placed at 4° C. for 15-30 minutes. The filters were processed as described by Maniatis, L., Fritsch, E. F. and Sambrook, 3. (1982) Molecular Cloning: A Laboratory Manual, Cold Spring Harbor. The baked filters were wetted with 2x SSC and prehybridized for two or more hours in a solution of 150mm Tris-Cl(8.0), 750mM NaCl, 10mM EDTA, 5x Denhardt's, 0.1% SDS and 0.1% sodium pyrophosphate in a sealed cooking bag at room temperature. The prehybridization solution was removed and replaced with fresh solution containing $1 \times 10^6$ cpm/ml solution $^{32}$P-labeled oligonucleotide. Hybridization was carried out at room temperature for 2-20 hours. The filters were then washed with 6X SCC, 0.1% SDS and 0.01M sodium phosphate (pH 7.2) for 20-30 minutes at increasing temperatures with autoradiography after each temperature change for one hour at $-80°$ C. with two intensifying screens. The final washing temperature was based on the equation: $T_m = 2.20$ C.$\times$(the number of A-T bases)+4° C.$\times$(the number of G-C bases) pursuant to Hanahan, D. and Meselson, M. (1983) Methods Enzym. 100,333-342. It was observed that the wild-type was usually off at $T_m - 10°$ C.

EXAMPLE 9

Isolation of ds mutant

Single, well-isolated positives were removed into 5 ml YT with 50ul exponential JM101 as well as streaked into a YT plate with a JM101 lawn. The cultures were incubated at 37° C. with aeration for six to eight hours and then centrifuged at 3,000rpm for ten minutes at 4° C. ds DNA was isolated as described in Manjarls, L., Fritsch, E. J. and Sambrook, J. (1982) Molecular Cloning: A Laboratory Manual, Cold Spring Harbor. If possible, mutations are confirmed by restriction digests. If not, the screening procedure is (ideally) repeated on the streaked plates. A large culture of the proposed mutant ds DNA was prepared pursuant to the method described in Maniatis, p. 90.

EXAMPLE 10

DNA Sequencing

The double-stranded mutant DNA was then digested with the appropriate restriction enzymes and isolated from polyacrylamide gels. These fragments were end-labeled and sequenced by the method described by Maxam, A. M. and Gilbert, N. (1980) Methods Enzym. 65, 499–560. Alternatively, the fragments can be subcloned into M13 or pUC vectors and sequenced by the dideoxy method described by Sanger, J., Nicklen, S. and Coulson, A. R. (1977) Proc. Natl. Acad. Sci. U.S.A 74, 5463–5467.

Transfection of mammalian cells and selection of a cell line produced by the above procedures can then be expressed by the following procedure: The mutant ds DNA can be ligated with Bam linkers and inserted into a bovine papilloma virus (BPV) expression cassette that includes the BPV genome, the mouse metallothionein promoter and SV40 poly (A) sequences as per Hsiung et. al. (1984) J. Mol. Applied Genetics 2,497. Mouse epithelioid cells (C127) may then be transfected using the calcium phosphate precipitation method. Transformed cells are ideally identified 10–14 days after transfection by their piled-up appearance. Foci of cells should then be subcloned to obtain a pure population and cultured in Dulbecco's Modified Eagle's Medium (DMEM) supplemented with 2% fetal bovine serum. Mutant hCG secreted into the culture medium will be purified by a three step process that included Tris Acryl Blue chromotography, ion exchange and gel filtration chromotography. Activity can be monitored through the purification process by a radioimmunoassay kit available for this purpose from Serono Laboratories.

The cell line that expresses the greatest amount of mutant hCG will stimulate the secretion of testosterone from suspension cultures of Leydig cells. Leydig cells can be obtained from adult male mice testes. Approximately $0.25\times10^6$ Leydig cells are ideally incubated in approximately 1 ml (DMEM) that contains one of several dose levels of native hCG added to the cells. A half-maximal dose of hCG may then be readily determined. A second set of suspension cultures should then be treated with a half-maximal dose of hCG and one of several increasing doses of the mutant recombinant hCG. A biologically inactive form of hCG will compete for binding to the receptor upon the Leydig cells and decrease the testosterone response of the native form.

Following the determination of the dose relationship between native and mutant hCG necessary to completely inhibit the native hCG-induced testosterone response, the mutant form can then be readily tested for its ability to induce abortion in a variety of species reported to secrete a chorionic gonadotropin, including the rhesus monkey and the optional antagonist hormone selected in accordance with the principles of the present invention.

From the foregoing, one skilled in the art will readily appreciate that numerous departures and variations may be made, particularly with respect to the specific procedures outlined without departing from the spirit or scope of the present invention.

What is claimed is:

1. A recombinant DNA molecule comprising a nucleotide sequence that encodes a glycoprotein hormone which is a modification of a native glycoprotein hormone selected from the group consisting of luteinizing hormone, follicle stimulating hormone, thyroid stimulating hormone, and chorionic gonadotropin, said modification comprising complete elimination of at least one N-linked oligosaccharide chain such that the modified hormone exhibits approximately the same receptor binding capacity and plasma half-life as the native glycoprotein hormone and has sufficiently low biological activity to permit its use as a competitive antagonist, and wherein said nucleotide sequence differs from the nucleotide sequence of the DNA molecule encoding the corresponding native glycoprotein hormone in a manner which causes said modification in the glycoprotein hormone encoded thereby.

2. The recombinant DNA molecule of claim 1 wherein said nucleotide sequence encodes human glycoprotein hormone having a N-linked oligosaccharide chain eliminated from amino acid position 52 and/or 78 of the alpha subunit thereof.

3. A method of producing a modified glycoprotein hormone selected from the group consisting of luteinizing hormone, follicle stimulating hormone, thyroid stimulating hormone, and chorionic gonadotropin, and said glycoprotein hormone having at least one N-linked oligosaccharide chain completely eliminated therefrom to form said modified glycoprotein hormone such that the modified hormone exhibits approximately the same receptor binding capacity and plasma half-life as the native glycoprotein hormone and has sufficient low biological activity to permit its use as a competitive antagonist, which method comprises culturing a host cell transfected with the recombinant DNA molecule of claim 1, and purifying said hormone from the culture.

4. The method of claim 3 wherein said recombinant DNA molecule encodes human glycoprotein hormone wherein having a N-linked oligosaccharide chain eliminated from amino acid position 52 and/or 78 of the alpha subunit thereof.

* * * * *